US009355889B2

(12) United States Patent
Waldron (10) Patent No.: US 9,355,889 B2
(45) Date of Patent: May 31, 2016

(54) SEMICONDUCTOR-ON-INSULATOR DEVICE AND METHOD OF FABRICATING THE SAME

(71) Applicant: IMEC VZW, Leuven (BE)

(72) Inventor: Niamh Waldron, Leuven (BE)

(73) Assignee: IMEC VZW, Leuven (BE)

( * ) Notice: Subject to any disclaimer, the term of this patent is extended or adjusted under 35 U.S.C. 154(b) by 0 days.

(21) Appl. No.: 14/673,517

(22) Filed: Mar. 30, 2015

(65) Prior Publication Data

US 2015/0279725 A1    Oct. 1, 2015

(30) Foreign Application Priority Data

Mar. 28, 2014   (EP) ..................................... 14162371

(51) Int. Cl.
| | |
|---|---|
| H01L 21/762 | (2006.01) |
| H01L 29/16 | (2006.01) |
| H01L 29/161 | (2006.01) |
| H01L 29/201 | (2006.01) |
| H01L 29/06 | (2006.01) |
| H01L 29/34 | (2006.01) |
| H01L 21/84 | (2006.01) |
| C12N 15/82 | (2006.01) |

(52) U.S. Cl.
CPC ...... *H01L 21/76251* (2013.01); *C12N 15/8201* (2013.01); *C12N 15/8241* (2013.01); *C12N 15/8261* (2013.01); *H01L 21/76264* (2013.01); *H01L 21/845* (2013.01); *H01L 29/0649* (2013.01); *H01L 29/16* (2013.01); *H01L 29/161* (2013.01); *H01L 29/201* (2013.01); *H01L 29/34* (2013.01)

(58) Field of Classification Search
CPC . H01L 21/76251; H01L 29/34; H01L 29/201; H01L 21/76264; H01L 29/161; H01L 29/0649; H01L 29/16
See application file for complete search history.

(56) References Cited

PUBLICATIONS

Takagi et al in the article "III-V-on-Insulator MOSFETs on Si substrates fabricated by direct wafer bonding" in ECS Transactions, 33 (4) p. 359-370 (2010).

*Primary Examiner* — David Vu
(74) *Attorney, Agent, or Firm* — Knobbe, Martens, Olson & Bear LLP (57) ABSTRACT

The disclosed technology generally relates to semiconductor-on-insulator (SOI) devices and more particularly to SOI devices having a channel region comprising a Group III-V or a Group IV semiconductor material, and also relates to methods of fabricating the same. In one aspect, a method comprises providing a pre-patterned donor wafer, providing a handling wafer and bonding the pre-patterned donor wafer to the handling wafer by contacting the first oxide layer to the handling wafer. Providing a pre-patterned donor wafer comprises providing a donor substrate comprising a first semiconductor material, forming shallow trench isolation (STI) regions in the donor substrate, and forming fins in the donor substrate in between the STI regions, where each fin comprises a Group III-V or Group IV semiconductor material that is different from the first semiconducting material and laterally extends in a direction parallel to a major surface of the donor substrate and between the STI regions. Providing the pre-patterned donor wafer additionally includes providing a first oxide layer overlying the STI regions and the fins. After bonding the donor wafer to the handling wafer, at least part of the first semiconducting material of the pre-patterned donor wafer is removed and the STI regions and the fins are thinned thereby forming channel regions comprising the Group III-V or Group IV semiconductor material.

9 Claims, 7 Drawing Sheets

SEMICONDUCTOR-ON-INSULATOR DEVICE AND METHOD OF FABRICATING THE SAME

CROSS-REFERENCE TO RELATED APPLICATIONS

This application claims foreign priority to European application EP 14162371.3, filed Mar. 28, 2014, the content of which is incorporated by reference herein in its entirety.

BACKGROUND

1. Field

The disclosed technology generally relates to semiconductor-on-insulator (SOI) devices and more particularly to SOI devices having a channel region comprising a Group III-V or a Group IV semiconductor material, and also relates to methods of fabricating the same.

The present disclosure also relates to a SOI wafer suitable for manufacturing such semiconductor-on-insulator devices.

The present disclosure also relates to a donor wafer for manufacturing a semiconductor-on-insulator wafer and associated SOI devices.

2. Description of the Related Technology

The semiconductor industry has been considering materials other than silicon (Si) as a base semiconductor material for various integrated circuit devices, in order to maintain or improve their cost and performance, as well as providing scaling options for future technology nodes. Possible candidates to replace or add to Si as the base semiconductor material, e.g., as channel material for transistor devices include other semiconductor materials of group IV, e.g., germanium (Ge) and silicon-germanium (SiGe), and compound semiconductors, e.g., group III-V alloy semiconductor materials (also referred to herein as III-V materials). To be cost-competitive, III-V materials should be capable of being monolithically integrated with Si, in order to benefit from various existing Si-based semiconductor processing techniques and infrastructure. The use of Si as a substrate would also enable the integration of several functional blocks on the same platform, such as for example logic, high-frequency, and 110 circuitry.

The integration of III-V materials on a Si platform, however, poses various technological challenges, e.g., defects arising from the integration. Some defects may arise, for example, from a lattice mismatch between silicon and various III-V materials or between the various III-V materials themselves, such as, e.g., anti-phase boundaries, mismatch stress relaxation, threading dislocations and stacking faults, to name a few.

One approach of integrating III-V materials on a Si platform is a technology referred to as III-V-on-insulator (III-V-OI) technology, which has been suggested as a promising technology for advanced CMOS applications for 1×nm technology node and beyond.

Some methods of fabricating III-V-OI structures have been described Takagi et al in the article "III-V-on-Insulator MOSFETs on Si substrates fabricated by direct wafer bonding" in ECS Transactions, 33 (4) p.359-370 (2010). A first method involves direct growth of III-V materials on Si substrates. This method has the disadvantage of using thick buffer layers (on the order of 1 μm and more) in order to keep the crystal quality of the III-V layer as high as possible and the defect level at the interface as low as possible. The use of thick buffer layers (also often referred to as strain relaxed buffer (SRB) layers) is moreover very expensive. A second method is known as direct wafer bonding (DWB). In this approach, an InGaAs layer is thereby formed on a 2 inch InP donor wafer. A buried oxide (BOX) layer of $SiO_2$ is then deposited on the InGaAs/InP. The $SiO_2$/InGaAs/InP wafer is then bonded in air to a Si handling wafer. The InP donor wafer is thereafter removed resulting in a III-V-OI on Si substrate wafer which may be further processed.

This method has the disadvantage that the use of 2 inch III-V donor wafers is not a feasible solution for the 1×nm technology node and beyond, which will be based on substrate platforms that are at least 12 inches (300 mm). Moreover, 2 inch III-V donor wafers can be prohibitively expensive.

SUMMARY OF CERTAIN INVENTIVE ASPECTS

It is an aim of at least some as aspects of the present disclosure to provide a method for manufacturing semiconductor-on-insulator devices.

It is an aim of the present disclosure to provide a semiconductor-on-insulator wafer and a method for manufacturing such a semiconductor-on-insulator wafer. The semiconductor-on-insulator wafer from the present disclosure may be used for manufacturing semiconductor-on-insulator devices.

It is an aim of the present disclosure to provide a donor wafer for manufacturing a semiconductor-on-insulator wafer and more specifically for manufacturing semiconductor-on-insulator devices.

This aim is achieved according to at least some embodiments of the disclosure with a method showing the technical characteristics.

According to a first aspect, a method for manufacturing semiconductor-on-insulator devices is disclosed. The method comprises providing a pre-patterned donor wafer, which preferably comprises the steps of providing a donor substrate comprising a first semiconductor material; forming shallow trench isolation (STI) regions in the donor substrate; forming fins (also referred to as fin structures) in the donor substrate in between the STI regions, the fins comprising a Group III-V or a Group IV semiconductor material (both different from the first semiconducting material), the fins extending from the donor substrate separated by and in between the STI regions. The pre-patterned donor wafer thus preferably comprises a donor substrate, STI regions or structures provided on the donor substrate, and fins in between the STI regions, the fins comprising a Group III-V or a Group IV semiconductor material (both different from the first semiconducting material), the fins extending from the donor substrate separated by and in between the STI regions. The method further comprises providing a first oxide layer overlying the STI regions and the fins; providing a handling wafer; bonding the (front side of the) pre-patterned donor wafer to the handling wafer by contacting the oxide layer to the handling wafer; removing (e.g. comprising thinning (e.g. parallel thinning) and/or etching) at least part of the first semiconductor material of the pre-patterned donor wafer (from its back side) and, preferably thereafter, thinning the STI regions and the fins thereby forming channel regions comprising the Group III-V or Group IV semiconductor material.

According to embodiments of the first aspect the fins are formed by replacing at least part of the first semiconductor material of the donor substrate in between the STI regions by the Group III-V or the Group IV semiconductor material. The first semiconductor material in between the STI regions may thus be removed partially (not reaching the depth of the STI structures) or completely (reaching the full depth of the STI structures). Removing the first semiconductor material is preferably done by etching. The group III-V or the Group IV semiconductor material is preferably provided by epitaxial growth in between the STI regions starting from the first semiconductor material. The mechanism of replacing the first semiconductor material into the Group III-V or the Group IV semiconductor material is also generally known as aspect ratio trapping (ART) technique. The replacing is preferably a regrowth of the protrusions in the trenches in between the STI structures. The aspect ratio trapping effects reduced the formation of defects during such a regrowth process.

According to embodiments of the first aspect, the remaining STI regions may be removed after forming the channel regions.

According to embodiments of the first aspect, providing a handling wafer comprises providing a handling substrate comprising a second semiconductor material and providing another, a second oxide layer on the handling substrate. Bonding then preferably comprises bonding the first oxide layer to the second oxide layer.

Both the donor substrate and the handling substrate preferably comprise silicon (Si), but other for the skilled person suitable materials can be used.

The donor substrate is preferably a blanket Si wafer, but other for the skilled person suitable substrates can be used.

The handling substrate is preferably chosen from a blanket or patterned Si wafer, a blanket or patterned Ge wafer, a blanket or patterned SOI wafer, a blanket or patterned germanium-on-silicon wafer, or a blanket or patterned GeOI wafer.

According to embodiments of the first aspect the donor wafer and the handling wafer have a wafer size of at least 300 mm.

The first oxide layer and the second oxide layer are preferably chosen from an insulating metal oxide (e.g. $Al_2O_3$, $HfO_2$), an insulating dielectric layer (e.g. SiO, SiN), or an insulating wide bandgap semiconductor (e.g. AN). In preferred embodiments, the first oxide layer is an $Al_2O_3$ layer and the second oxide layer is a $SiO_2$ layer.

According to embodiments of the first aspect, removing at least part of the first semiconductor material of the pre-patterned donor wafer is done from the back side of the pre-patterned donor wafer.

According to embodiments of the first aspect, removing the donor substrate of the pre-patterned donor wafer may comprise a first (rough or non-selective; e.g. based on planar thinning technique) removal step followed by a second (selective; e.g. based on selective etch) removal step. The first removal step can remove the first semiconductor material of the donor substrate below the STI regions (i.e. remaining at a level above the STI structures, without reaching or affecting the STI structures) at the backside of the pre-patterned donor wafer). The second removal step removes the remaining first semiconductor material of the semiconductor substrate, including at least a portion in between the STI regions, if present (i.e. of the fins).

The removal step preferably comprises a thinning step by means of a planar thinning technology/technique. The removal step may further comprise an etching step to remove the remaining material of the donor substrate (Si substrate), selective with respect to the STI structures and the group III-V or the group IV material.

According to embodiments of the first aspect, the STI regions are formed by patterning the donor substrate thereby forming STI trenches and providing a dielectric material in the STI trenches. The dielectric material may be provided using state of the art deposition techniques. The dielectric material preferably comprises an oxide, e.g. $SiO_2$.

According to embodiments of the first aspect, the Group III-V semiconductor material is chosen from InP, InGaAs, InAs, GaAs, or GaAsSb. The Group IV semiconductor material is chosen from Ge or SiGe.

According to alternative embodiments of the first aspect, removing the donor substrate of the pre-patterned donor wafer may be done by hydrogen release implantation, which involves the implantation of hydrogen to a predetermined depth into the pre-patterned donor wafer before the step of bonding and thereafter releasing the donor substrate of the pre-patterned donor wafer at the predetermined depth of the hydrogen implantation, by for instance applying an anneal step (this process if known to the skilled person as process of the "smartcut" type). The anneal step can be performed only at the stage that the donor substrate is removed. The predetermined depth may be below the STI regions (i.e. remaining at a level above the STI structures, without reaching or affecting the STI structures) or may be (at a level) within the STI regions.

According to embodiments of the first aspect, thinning the STI regions and the fins is done simultaneously by chemical mechanical polishing (CMP).

According to embodiments, the fins have a defectivity level less than $10^9$ defects/$cm^2$, more preferably less than $10^6$ defects/$cm^2$.

According to embodiments, the upper portions of the fins (the portion originally most removed from the donor substrate; or the portion near the first oxide layer) have a defectivity level less than $10^9$ defects/$cm^2$, more preferably less than $10^6$ defects/$cm^2$.

According to a second aspect of the present disclosure, a pre-patterned donor wafer for manufacturing a semiconductor-on-insulator device is disclosed, comprising a donor substrate comprising a first semiconductor material; a pattern of shallow trench isolation (STI) regions and fins on the donor substrate; the fins being separated by and located in between the STI regions; the fins comprising at least an upper part of a Group III-V or Group IV semiconductor material being different of the first semiconductor material, and a first oxide layer overlying the pattern.

According to embodiments, the donor substrate is a blanket Si wafer. The donor substrate preferably has a wafer size of at least 300 mm.

According to embodiments, the Group III-V semiconductor material is preferably chosen from InP, InGaAs, InAs, GaAs, or GaAsSb.

According to embodiments, the Group III-V semiconductor material is chosen from InP, GaAs, InAs, AlAs, GaSb, AlSb, InSb and all ternary and quaternary combinations thereof.

The Group IV semiconductor material is preferably chosen from Ge or SiGe.

According to embodiments, the at least upper part of the fins (the portion adjacent to the first oxide layer) has a defectivity level less than $10^9$ defects/$cm^2$, more preferably less than $10^6$ defects/$cm^2$. This portion can preferably serve as a channel structure/layer for a semiconductor device.

According to embodiments, a bottom part (e.g. the portion away from the first oxide layer) of the fins comprises the first semiconductor material.

According to embodiments, the fins further comprise below the upper part, and above the bottom part (or in between the upper part and the bottom part) another Group III-V or Group IV semiconductor material.

According to embodiments, the first oxide layer comprises an insulating metal oxide, an insulating dielectric layer, or an insulating wide bandgap semiconductor. The first oxide layer is preferably chosen from an insulating metal oxide (e.g.

Al$_2$O$_3$, HfO$_2$), an insulating dielectric layer (e.g. SiO, SiN), or an insulating wide bandgap semiconductor (e.g. AlN).

According to a third aspect of the present disclosure, a semiconductor-on-insulator wafer is disclosed, comprising a semiconductor substrate, an oxide layer on the substrate and a pattern of fins and STI regions or structures on the (then buried) oxide layer, the fins comprising a Group III-V or a Group IV semiconductor material different from the semiconductor substrate, the fins being in between, e.g. separated by and located in between, the STI regions or structures.

According to embodiments, the semiconductor-on-insulator wafer has a wafer size of 300 mm or larger. Preferably the semiconductor substrate is a Si-based substrate.

According to embodiments, the Group III-V semiconductor material is chosen from InP, InGaAs, InAs, GaAs, or GaAsSb.

According to embodiments, the Group III-V semiconductor material is chosen from InP, GaAs, InAs, AlAs, GaSb, AlSb, InSb and all ternary and quaternary combinations thereof.

According to embodiments, the Group IV semiconductor material is chosen from Ge or SiGe.

According to embodiments, the oxide layer comprises insulating metal oxide, an insulating dielectric layer, an insulating wide bandgap semiconductor. The oxide layer can comprise a plurality of oxide layers. It can for instance be a bilayer of a first oxide layer, attached/adjacent to the fins, and a second oxide layer at the other side of the first oxide layer, the second oxide layer separating the first oxide layer from the semiconductor substrate. The first oxide layer and the second oxide layer are preferably chosen from an insulating metal oxide (e.g. Al$_2$O$_3$, HfO$_2$), an insulating dielectric layer (e.g. SiO, SiN), or an insulating wide bandgap semiconductor (e.g. AN). In preferred embodiments, the first oxide layer is an Al$_2$O$_3$ layer and the second oxide layer is a SiO$_2$ layer.

According to embodiments, the fins have a defectivity level less than $10^9$ defects/cm$^2$, more preferably less than $10^6$ defects/cm$^2$.

According to embodiments, the upper portions of the fins (the portion near the first oxide layer) have a defectivity level less than $10^9$ defects/cm$^2$, more preferably less than $10^6$ defects/cm$^2$.

It is an advantage of embodiments of the present disclosure that III-V-based semiconductor device may be formed with defect-free active channel region or at least a III-V-based semiconductor device with reduced defects in the active channel region, i.e. defect level less than $10^9$ defects/cm$^2$, more preferably less than $10^6$ defects/cm$^2$.

It is an advantage of embodiments of the present disclosure that III-V-OI on Si semiconductor devices may be manufactured using a full wafer approach, i.e. using wafer of at least 300 mm (also referred to as '12 inch') wafer size.

It is an advantage of embodiments of the present disclosure that manufacturing costs are reduced since a III-V-OI wafer of at least 300 mm is provided. By using pre-patterned donor wafers (using ART process for manufacturing thereof), thinner layers are grown (i.e. layers thinner than 300 nm or smaller), only on certain areas of the wafer thereby substantially reducing costs compared to prior art techniques where III-V material has to be provided over the whole wafer.

It is an advantage of embodiments of the present disclosure that III-V materials may be integrated on Si monolithically using Si wafers as handling and device wafer without the use of expensive and small III-V wafers and/or without the use of expensive and thick strain relaxed buffer (SRB)-based substrates. It is thus an advantage of embodiments of the present disclosure that the method for forming III-V-OI on Si semiconductor devices is less expensive than methods as known for a person skilled in the art.

It is an advantage of embodiments of the present disclosure that III-V semiconductor device may be provided with a better electrostatic control and Vt control by substrate voltage.

It is an advantage of embodiments of the present disclosure that co-integration of different semiconductor materials on a single wafer is possible.

BRIEF DESCRIPTION OF THE DRAWINGS

The disclosure will be further elucidated by means of the following description and the appended figures.

The drawings described are only schematic and are non-limiting. In the drawings, the size of some of the elements may be exaggerated and not drawn on scale for illustrative purposes. The dimensions and the relative dimensions do not necessarily correspond to actual reductions to practice of the disclosure.

DETAILED DESCRIPTION OF CERTAIN ILLUSTRATIVE EMBODIMENTS

The present disclosure will be described with respect to particular embodiments and with reference to certain drawings but the disclosure is not limited thereto but only by the claims.

Furthermore, the terms first, second, third and the like in the description and in the claims, are used for distinguishing between similar elements and not necessarily for describing a sequential or chronological order. The terms are interchangeable under appropriate circumstances and the embodiments of the disclosure can operate in other sequences than described or illustrated herein.

Moreover, the terms top, bottom, over, under and the like in the description and the claims are used for descriptive purposes and not necessarily for describing relative positions. The terms so used are interchangeable under appropriate circumstances and the embodiments of the disclosure described herein can operate in other orientations than described or illustrated herein.

Furthermore, the various embodiments, although referred to as "preferred" are to be construed as example manners in which the disclosure may be implemented rather than as limiting the scope of the disclosure.

According to a first aspect, illustrated in FIGS. 1 to 13, a method for manufacturing semiconductor-on-insulator devices 3 is disclosed.

FIG. 1 to FIG. 4 schematically illustrates intermediate structures at different process stages according to embodiments of the present disclosure for providing a pre-patterned donor wafer 1. The pre-patterned donor wafer 1 can be provided using a technique referred to herein as an aspect ratio trapping (ART) process. The ART process involves forming high aspect ratio sub-micron trenches to trap threading dislocations, thereby greatly reducing the dislocation density of lattice mismatched materials grown on silicon, as described below.

Figure 1:
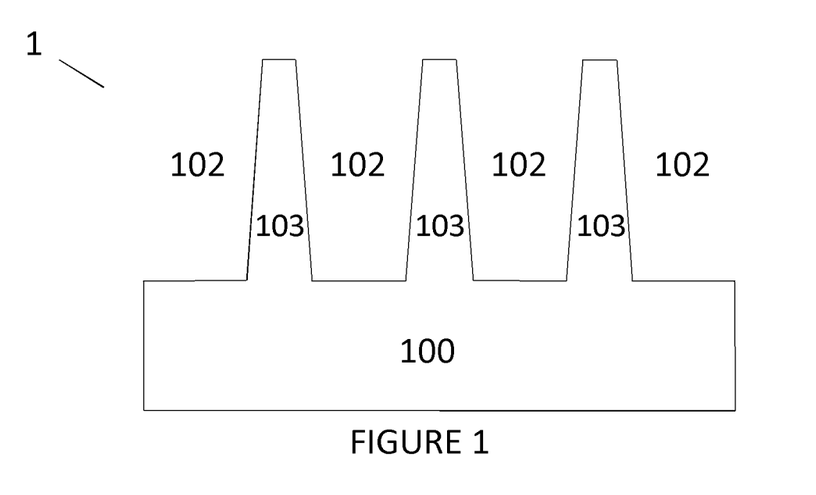
FIGS. 1-13 illustrate intermediate semiconductor structures of a semiconductor-on-insulator at various processing stages of a method of fabricating according to various embodiments.

Referring to FIG. 1, a semiconductor substrate 100 is provided. The semiconductor substrate is a donor substrate comprising a first semiconductor material, which can be a Si-based substrate. As used herein, a Si-based substrate can be a Si substrate or include other group IV elements, e.g., Ge, C or Sn, as well as suitable dopants, such, e.g. P, B. The semiconductor substrate 100 can be a wafer with wafer size of at least 300 mm (also referred to as a 12 inch wafer). Also larger wafer sizes may be used for the donor substrate, such as for example 450 mm wafers (also often referred to as 18 inch wafer). A plurality of etched regions 102, e.g., trenches, extending in a first direction, are formed in the substrate 100, thereby forming fins or lines 103 between adjacent etched regions 102.

Figure 2:
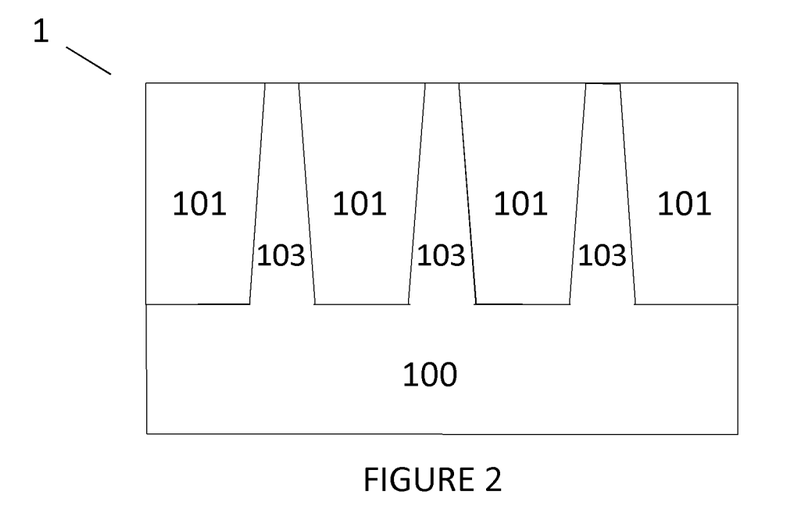

Referring to FIG. 2, the etched regions 102 are filled with a suitable dielectric, e.g., $SiO_2$, to form shallow trench isolation (STI) regions 101 in the donor substrate 100 (FIG. 2). In various embodiments, the STI regions 101 may have a depth between about 100 nm and about 500 nm or between about 100 nm and about 300 nm, and may have a width between about 500 nm and about 20 nm, between about 300 nm and about 20 nm or between about 100 nm and about 20 nm. For more advanced STI modules, the depth of the STI region can even be below 100 nm, e.g., between about 100 nm and about 10 nm or between about 50 nm about 10 nm, and the width of the STI region can be down to 5 nm, e.g., between about 20 nm and about 5 nm or between about 10 nm and about 5 nm. In various embodiments, the aspect ratio (defined herein as the ratio between the depth and the width) of the STI regions 101 exceeds 2, e.g., between about 2 and 25 or between about 5 and 25. Providing the STI regions 101 may be done by techniques known by a person skilled in the art. For instance in may include lithographic patterning the semiconductor substrate 100, etching the semiconductor substrate 100 (FIG. 1) and thereafter filling the etched regions 102 with an insulating material such as for example an oxide (for example $SiO_2$)(FIG. 2).

After providing the STI regions 101, fins or lines 103 of the first semiconductor material of the donor substrate 100 are present in between the STI regions 101. In the illustrated embodiment, the semiconductor fins or lines 103 have a height equal to the height of the STI regions 101, and a width of the fins or lines 103 range between about 100 nm and about 20 nm, or between about 20 nm and about 5 nm. As a rule of thumb, the aspect ratio (defined herein as the ratio between the depth and the width) of the fins exceed about 2, e.g., between about 2 and 25 or between about 5 and 25. The semiconductor fins or lines 103 are elongated and lying in a same plane as the semiconductor substrate surface. The length of the semiconductor fins or lines may be several nm's, preferably much larger than the width of the fin, for example 10 times larger. A pattern of STI regions 101 and fins or lines 103 is thus provided in the donor substrate 100, wherein the fins or lines 103 are formed between the STI regions 101 and are laterally separated or isolated from each other. Such a structure with semiconductor fins or lines 103 formed between and separated by STI regions is also often referred to as a STI template structure.

Figure 3:
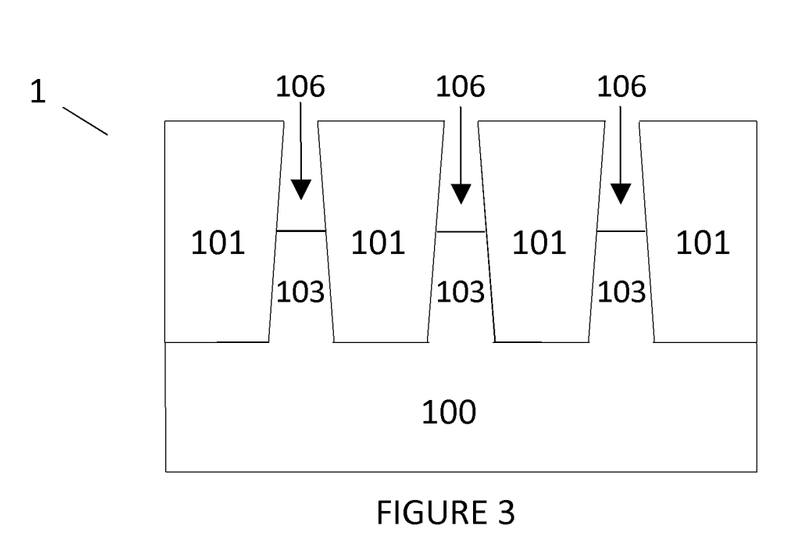
Figure 4:
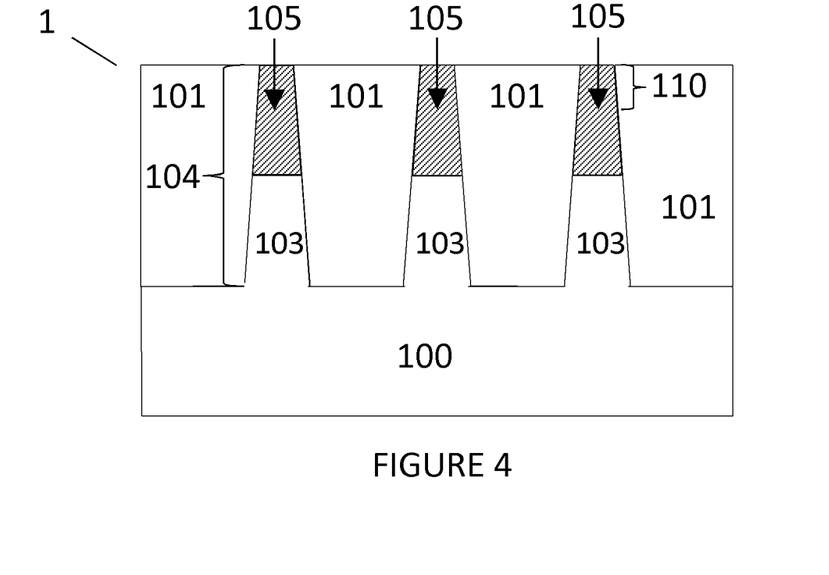

Referring to FIGS. 3 and 4, after providing the STI regions 101 (and semiconductor fins 103) at least part of the remaining first semiconductor material in between the STI regions 101 is replaced by a second semiconductor material 105, which may be a Group III-V or Group IV semiconductor material 105. The Group III-V or Group IV semiconductor material 105 is chosen to be different as the initial first semiconductor material of the substrate 100 and the fins or lines 103. As a result, fins 104 are formed on the semiconductor substrate 100 between adjacent STI regions 101, wherein the fins 104 now includes the second semiconductor material 105 different from the first semiconductor material of the fins or lines 103 and of the semiconductor substrate 100. In one embodiment, fins 104, for example, may include InP fins.

Referring to FIG. 3, replacing the first semiconductor material may be done by at least partly removing the first semiconductor material in between the STI regions 101 thereby creating cavities 106 between the STI regions 101. The fins 103 are thus recessed leaving cavities or recesses 106. Referring to FIG. 4, the cavities 106 are then filled with a second semiconductor material 105, e.g., with a Group III-V or Group IV semiconductor material different from the semiconductor material of the fins 103. In some embodiments, at least some of the individual cavities 106 may be filled with more than one Group III-V or Group IV semiconductor material. For example, some cavities may 106 may be filled with multilayers, such as for example, a bilayer of InGaAs/InP.

In yet other embodiments, at least some of the cavities 106 may be filled with a first Group III-V or Group IV semiconductor material while some other cavities may be filled with a second Group III-V or Group IV semiconductor material (which is different from the first Group III-V or Group IV semiconductor material). The second Group III-V or Group IV material can be formed in lieu of or in addition to the first Group III-V or Group IV material, according to different embodiments. For example, some of the recesses may be filled with InP, whereas some other recesses may be filled with Ge. The co-integration of different semiconductor materials for forming the fins 104 may be particularly advantageous for CMOS applications, e.g., where one material is used for NMOS transistors while another material is used for PMOS transistors. For example, InP fins may be used for a first type of semiconductor device (NMOS) and the Ge fins may be used for a second type of semiconductor device (PMOS). In some embodiments, the Group III-V or Group IV semiconductor material 105 of an NMOS may be under a compressive strain as-formed, while the second Group III-V or Group IV semiconductor material 105 of a PMOS may be under a tensile strain as-formed.

Referring to FIG. 3, the upper portions of the first semiconductor material of the fins 103 can be removed by dry or wet etching. Referring to FIG. 4, the recesses formed by the removal can subsequently be filled with the Group III-V or Group IV material by epitaxial growth, e.g., selective epitaxial growth, starting from the exposed semiconductor material of the donor substrate using ART. When grown by selective epitaxy, the Group III-V or Group IV material 105 is grown by bottom-up filling starting from the exposed semiconductor surface of the recessed fins 103, while growth is not initiated on the surfaces of the STI regions 101.

Similar to the fins 103 described above with respect to FIG. 2, the fins 104 in between the STI regions 101 preferably have an aspect ratio which is higher than 2. It will be appreciated that, by increasing the aspect ratio of the fins 104, the quality of the second semiconductor material is enhanced. More specifically, the higher the aspect ratio of the fins 104 the lower the defect density at the top part of the fins 104. Thus, a particular combination of the width and the height of the fins 104 is not a mere design choice to define a physical size, but instead, is instead a choice which qualitatively enhances the device performance by reducing defect density, e.g., dislocations within the volume of the fins 104.

Figure 5:
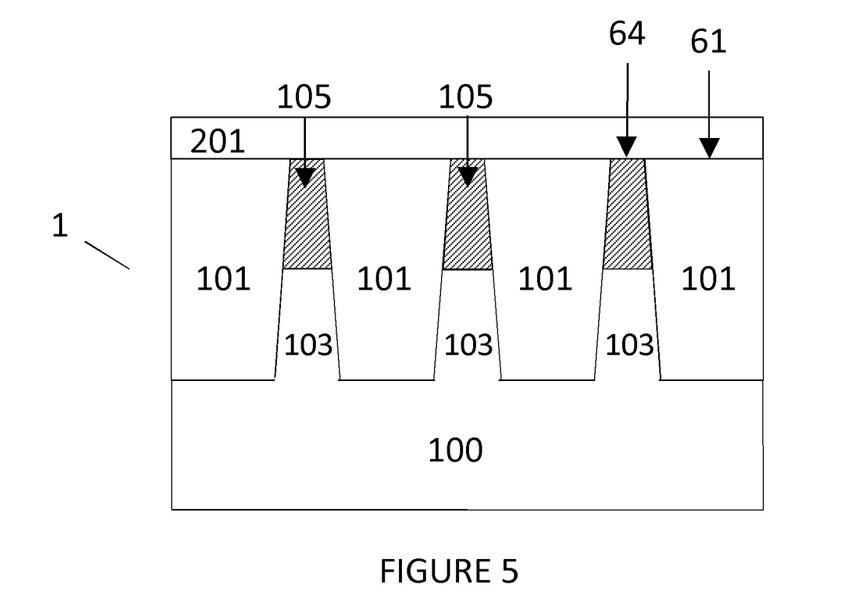

Referring to FIG. 5, vertical levels of top surfaces 61 of the STI regions and of top surfaces 64 of the final trenches/fin structures are substantially equal, e.g., at the same height level. The fins 104 and the STI regions 101 are thus abutting to form a substantially co-planar top surface 61.

For example, the donor substrate 100 may be a Si-substrate. SiO$_2$ STI regions 101 may be formed in the Si-substrate. At least top portions of the Si fins 103 between the STI regions may be replaced by InP. This may be done by etching at least part of the Si in between the STI regions and thereafter epitaxially growing InP in the etched regions on the semiconductor substrate using ART.

The top portions of the fins 104 which includes the Group III-V or Group IV semiconductor material 105 can serve as the active regions or channel regions 110 of the final semiconductor-on-insulator devices. These are the regions/portions of the fins which have the lowest defect density. In some embodiments, a defectivity level, or a defect density, of the top portions of the fins 104 is below $10^9$ defects/cm$^2$, more preferably below $10^6$ defects/cm$^2$.

Referring to FIG. 5, an (first) oxide layer 201 is formed on the pre-patterned donor wafer 1, i.e. on the top surface of the STI regions 101 and the final trenches 104/fins (103, 105) (FIG. 5). The first oxide layer 201 may be an insulating metal oxide (e.g. Al$_2$O$_3$, HfO$_2$), an insulating dielectric layer (e.g. SiO, SiN) or an insulating wide bandgap semiconductor (e.g. AN).

The first oxide layer 201 may be a bilayer for example an Al$_2$O$_3$/SiO bilayer wherein the Al$_2$O$_3$ layer serves to create a good interface with the channel regions and wherein the SiO serves to facilitate a better bonding with the handle wafer.

The first oxide layer 201 has a minimum thickness of about 2 to 3 nm such that the layer is closed and thus completely covering the underlying STI regions and fins, while having a maximum thickness of about 100 nm, depending on the device requirements. The oxide layer 201 can serve as a buried oxide layer (BOX layer) of the final semiconductor-on-insulator devices.

In some embodiments, the fins 104 may be passivated (such as for example using sulphur) before providing the (first) oxide layer 201. This may be done to improve the electrical interface between the pre-patterned donor wafer 1 and the oxide layer 201.

The first oxide layer 201 may be provided by deposition techniques known by a person skilled in the art such as for example chemical vapour deposition (CVD) or atomic layer deposition (ALD).

Figure 6:
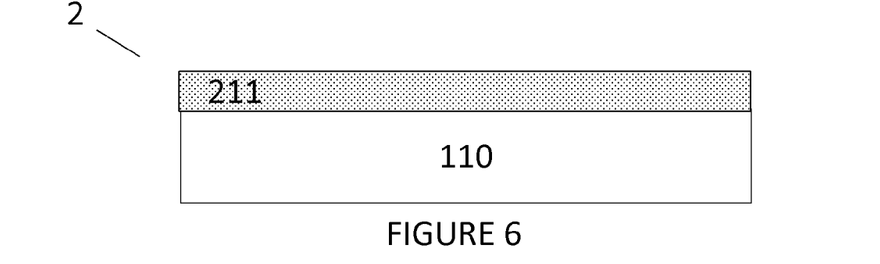

Referring to FIG. 6, a handling wafer 2 comprising a semiconductor substrate 110 is provided, which can have a second oxide layer 211 on top of the semiconductor substrate.

The second oxide layer 211 has the same or similar requirements as the first oxide layer and may be identical to the first oxide layer 201 (on the pre-patterned donor wafer 1). After bonding the pre-patterned donor wafer to the bonding wafer an interface (such as for example an interfacial oxide) may be present in between the first oxide layer and the second oxide layer.

In some embodiments, the semiconductor substrate 110 of the handling wafer 2 is a Si-based substrate. The handling wafer 2 can have a wafer size of at least 300 mm (12-inch wafers). Also bigger wafer sizes may be used, such as for example 450 mm wafers (18-inch wafers).

The handling wafer 2 can be, for example, a blanket Si wafer, a previously patterned Si wafer with Si active and/or Ge, SiGe active regions or can be for example a Ge-on-Si (patterned or blanket) wafer or a Ge—OI on Si (patterned or blanket) wafer.

Figure 7:
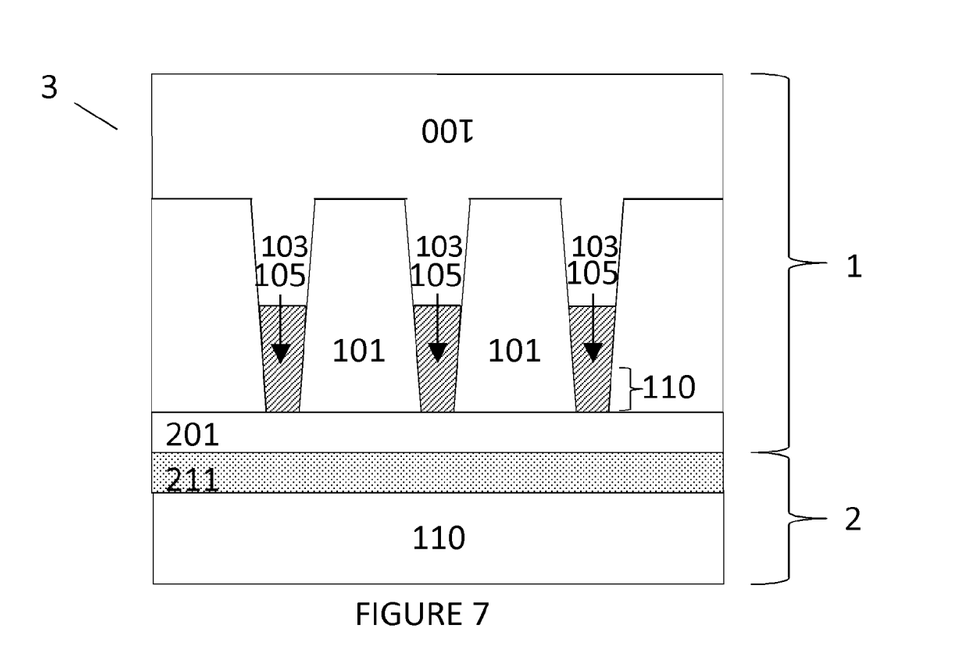

Referring to FIG. 7, the pre-patterned donor wafer 1 is bonded to the handling wafer 2 by contacting the oxide layer 201 of the pre-patterned donor wafer 1 to the handling wafer 2 or, if present, to the second oxide layer 211 on the handling wafer 2.

After bonding the front side of the pre-patterned donor wafer 1 to the handling wafer 2 (or the second oxide on the handling wafer), the pre-patterned donor wafer 1 is released which means the first semiconductor material 103 of the semiconductor substrate of the pre-patterned donor wafer 1 is removed. This may be done in a number of ways, as described below with respect to FIGS. 8-10.

Figure 8:
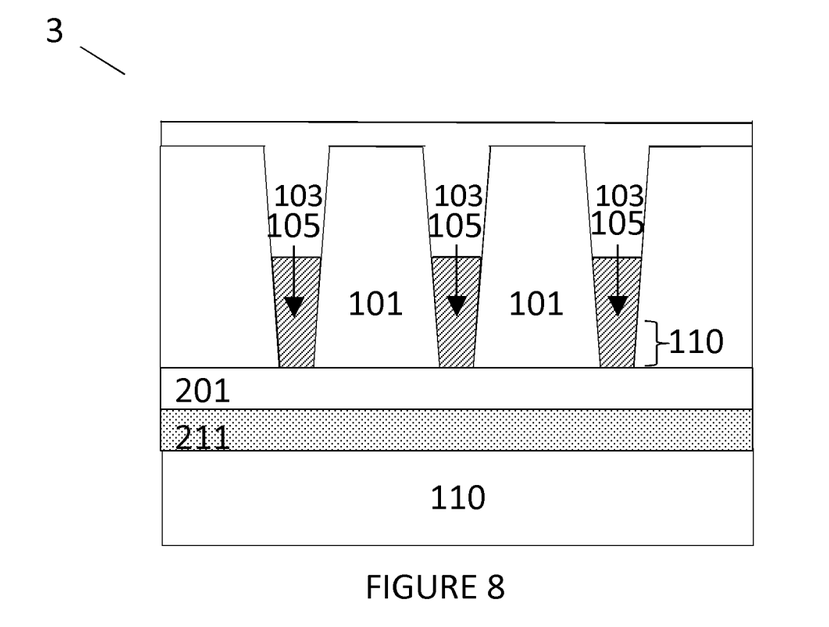
Figure 9:
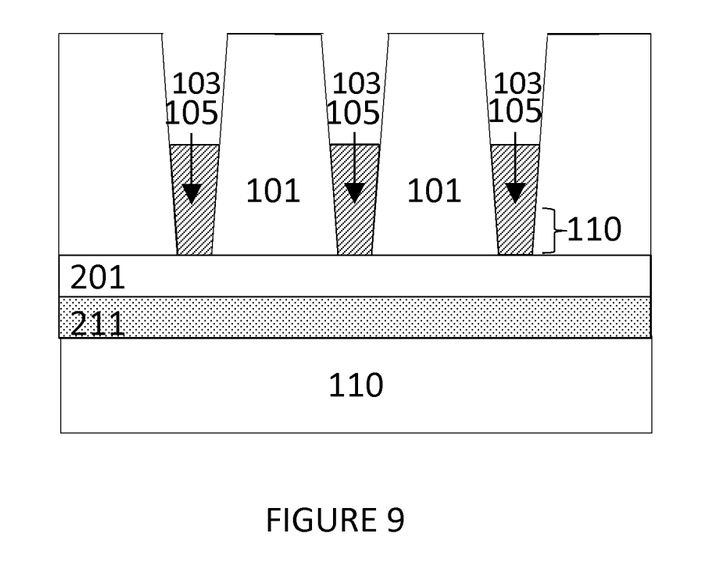

Referring to FIGS. 8 and 9, in one embodiment, releasing the pre-patterned donor wafer 1 includes a first (non-selective, e.g. by planar thinning process) removal process (FIG. 8) and a second (selective, e.g. by selective etching process) removal process (FIG. 9). In the first removal process of FIG. 8, a portion of the semiconductor material from the substrate 100 is removed from the backside of the wafer 1, e.g., the semiconductor substrate material below the STI regions 101. The substrate material 100 may be removed from the back side by a suitable process such as, e.g., grinding or polishing. In the second removal process of FIG. 9, the remaining semiconductor substrate material is removed, which may include the substrate material between the STI regions 101 in the fins 104. This may be done for example by wet etching (e.g. TMAH).

Figure 10:
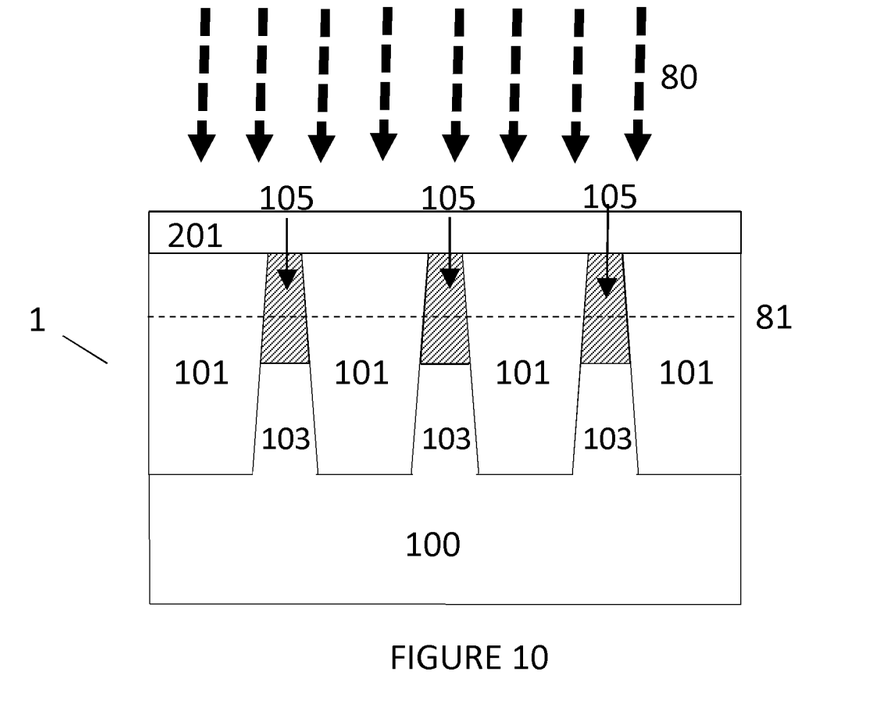
Figure 11:
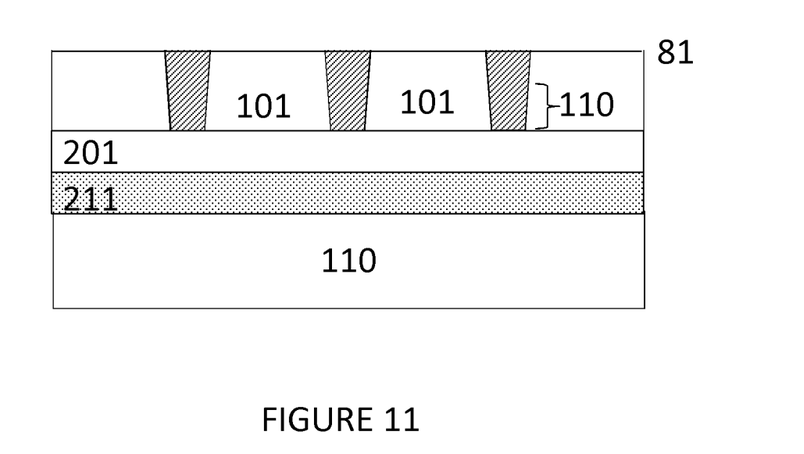

FIGS. 10 and 11 illustrates an alternative method of releasing the pre-patterned donor wafer 1, using a hydrogen (H) release implant. This process involves H$_2$ implantation 80 of the donor wafer to a predetermined depth 81 before the bonding step (FIG. 10). The predetermined depth 81 may be below the STI regions or may be in the STI regions. The depth of the H implant determines a vertical location where a subsequent separation of the pre-patterned donor wafer occurs, as illustrated in FIG. 11. As illustrated in FIG. 11, when the H-implanted wafer 1 is subsequently annealed, a separation occurs in the semiconductor material (Si) underneath the STI regions or directly in the STI regions itself. In the latter case there is only the STI material and the Group III-V or Group IV material remaining after the release.

If the separation occurs in the semiconductor material, the remainder of the semiconductor material (in the trenches) also needs to be removed. This may be done by selective etching.

Figure 12:
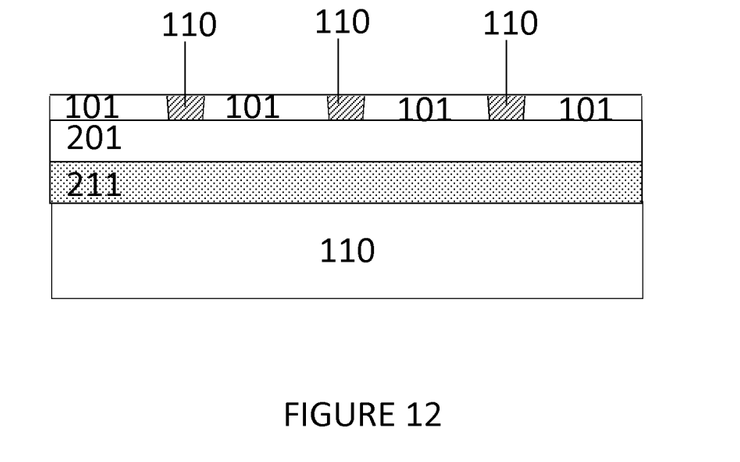

Referring to FIG. 12, after releasing the pre-patterned donor wafer, the remaining Group III-V or Group IV fins are thinned to the desired thickness according to embodiments. The Group III-V or Group IV material 105 in the fins is removed until that part is exposed which will serve as the active channel regions in the final semiconductor-on-insulator device. This can for instance be done by chemical mechanical polishing (CMP). Preferably a CMP process is used that uses a slurry which is non-selective to (i.e. is etching equally fast) the STI material and the Group III-V or the Group IV material.

The etching rate of the STI material and of the Group III-V or Group IV semiconductor material is preferably the same.

If a single layer has been originally grown in the trench, the CMP step will determine the final thickness of the channel region. If a bilayer was grown, e.g. InGaAs on InP, then the CMP can be stopped in the InP layer. The so-called buffer (i.e. InP) may be removed selectively by (wet) etching. In this way the thickness of the channel region is determined by its original thickness in the starting STI template wafer.

Figure 13:
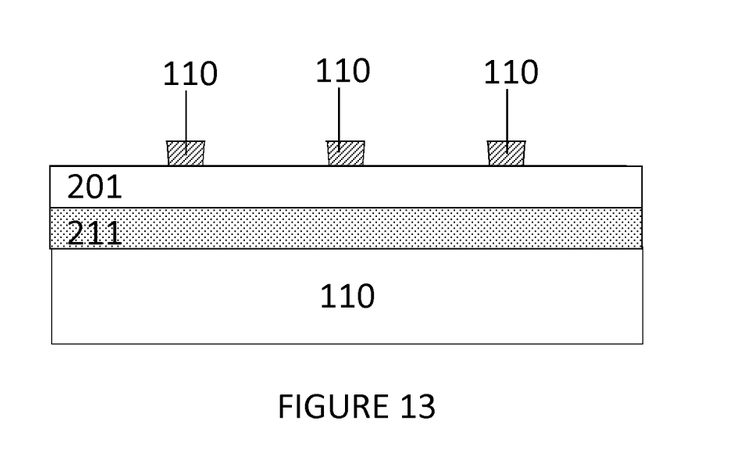

The remaining STI material from the STI regions 101 may optionally also be removed after thinning the final trenches (FIG. 13).

The STI material may also be kept to serve as an isolation layer and to maintain a planar surface.

As the active channel regions are now formed, further processing steps may be performed as known for a person skilled in the art to manufacture a semiconductor-on-insulator device, such as providing a gate stack, providing source/drain regions, providing contacting, etc.

According to aspects of the present disclosure, a semiconductor-on-insulator wafer suitable for manufacturing semiconductor-on-insulator devices is disclosed. More specifically a wafer with a wafer size of at least 300 mm or higher is disclosed comprising a group III-V or Group IV semiconductor material as active layer.

Therefore a pre-patterned donor wafer for bonding is disclosed, the donor wafer having also a wafer size of at least 300 mm or higher and comprising a patterned structure of trenches comprising the Group III-V or Group IV semiconductor material in between STI region. This is preferably achieved using aspect ratio trapping (ART).

According to a second aspect of the present disclosure, a pre-patterned donor wafer for manufacturing a semiconductor-on-insulator device is disclosed comprising
  a donor substrate comprising a first semiconductor material;
  a pattern of shallow trench isolation (STI) regions and fins on the donor substrate; the fins being separated by and located in between the STI regions; the fins comprising at least an upper part of a Group III-V or a Group IV semiconductor material being different of the first semiconductor material, and
  an oxide layer overlying the pattern (See FIG. 5).

According to a third aspect of the present disclosure, a semiconductor-on-insulator wafer is disclosed, comprising a semiconductor substrate, an oxide layer on the substrate and a pattern of fins and STI regions or structures on the oxide layer, the fins comprising a Group III-V or a Group IV semiconductor material different from the semiconductor substrate, the fins being in between, e.g. separated by and located in between, the STI regions or structures (see FIG. 11).

It is an advantage of the present disclosure that the layers grown are thinner (between 100 and 500 nm) compared to the techniques used in prior art (SRB layers are typically 1 µm thick). The layers are only grown on the patterned active part of the wafer (about 20-25% of the wafer area), which means the equivalent growth of the group III-V or Group IV semiconductor material is 10 to 50 times less compared to the use of SRB layers as is done in prior art. This has the advantage that manufacturing becomes less expensive as less group III-V or Group IV semiconductor material is used.

It is a further advantage of the present disclosure that defectivity in the active area is better compared to the defectivity level using SRB layers.

As the channel region is on a buried oxide layer and thus no buffer layer is used below the channel region as in prior art, a potential leakage path is not present.

While there has been illustrated or described what are presently considered to be example features, it will be understood by those skilled in the art that various other modifications may be made, or equivalents may be substituted, without departing from claimed subject matter. Additionally, many modifications may be made to adapt a particular situation to teachings of claimed subject matter without departing from central concept(s) described herein.

Therefore, it is intended that claimed subject matter not be limited to particular examples disclosed, but that claimed subject matter may also include all aspects falling within the possibility of appended claims, or equivalents thereof.

What is claimed is:

1. A method of fabricating a semiconductor-on-insulator device, the method comprising:
  providing a pre-patterned donor wafer, comprising:
    providing a donor substrate comprising a first semiconductor material,
    forming shallow trench isolation (STI) regions in the donor substrate,
    forming a plurality of fins, each fin formed between adjacent STI regions and separated from an adjacent fin by one of the STI regions, wherein a top part of each fin comprises a Group III-V or Group IV semiconductor material different from the first semiconductor material, and
    forming a first oxide layer over the STI regions and the fins;
  providing a handling wafer;
  bonding the pre-patterned donor wafer to the handling wafer by contacting the first oxide layer to the handling wafer;
  removing at least part of the first semiconductor material from a backside of the bonded pre-patterned donor wafer; and
  sufficiently thinning the STI regions and the fins from the backside of the bonded donor wafer to expose the Group III-V or Group IV semiconductor material, thereby forming channel regions comprising the Group III-V or Group IV semiconductor material.

2. The method of claim 1, wherein forming the fins comprises, after forming the STI regions, recessing at least an upper portion of the first semiconductor material between adjacent STI regions and epitaxially growing the Group III-V or Group IV semiconductor material in the recesses using an aspect ratio trapping process.

3. The method of claim 1, further comprising after thinning also removing remaining STI regions.

4. The method of claim 1, wherein providing the handling wafer comprises providing a handling substrate comprising a second semiconductor material covered with a second oxide layer.

5. The method of claim 1, wherein the donor substrate is a blanket Si wafer.

6. The method of claim 1, wherein the handling substrate is chosen from the group consisting of a blanket or patterned Si wafer, a blanket or patterned Ge wafer, a blanket or patterned SOI wafer, a blanket or patterned germanium-on-silicon wafer and a blanket or patterned GeOI wafer.

7. The method of claim 1, wherein the donor wafer and the handling wafer have the same wafer size, the wafer size being at least 300 mm in diameter.

8. The method of claim 1, wherein the Group III-V semiconductor material is chosen from the group consisting of InP, GaAs, InAs, AlAs, GaSb, AlSb, InSb and all ternary and quaternary combinations thereof, and wherein the Group IV semiconductor material is Ge or SiGe.

9. The method of claim 1, wherein removing at least part of the first semiconductor material comprises removing at least a portion of the first semiconductor material between the STI regions and a backside surface of the pre-patterned donor wafer, followed by further removing a remaining portion of the first semiconductor material between the STI regions.

* * * * *